(12) United States Patent
Cerman

(10) Patent No.: US 11,246,988 B2
(45) Date of Patent: Feb. 15, 2022

(54) BODY ARRANGEMENT FOR A DRUG DELIVERY DEVICE

(71) Applicant: Sanofi-Aventis Deutschland GMBH, Frankfurt am Main (DE)

(72) Inventor: Zdenek Cerman, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 84 days.

(21) Appl. No.: 16/316,965

(22) PCT Filed: Jul. 12, 2017

(86) PCT No.: PCT/EP2017/067508
§ 371 (c)(1),
(2) Date: Jan. 10, 2019

(87) PCT Pub. No.: WO2018/011254
PCT Pub. Date: Jan. 18, 2018

(65) Prior Publication Data
US 2019/0290854 A1     Sep. 26, 2019

(30) Foreign Application Priority Data

Jul. 14, 2016 (EP) .................................... 16179489

(51) Int. Cl.
*A61M 5/31* (2006.01)
*A61M 5/32* (2006.01)
*A61M 5/50* (2006.01)

(52) U.S. Cl.
CPC .............. *A61M 5/31* (2013.01); *A61M 5/321* (2013.01); *A61M 5/3202* (2013.01);
(Continued)

(58) Field of Classification Search
CPC .... A61M 2005/3256; A61M 2205/586; A61M 5/3243; A61M 5/3213; A61M 5/3275
See application file for complete search history.

(56) References Cited

U.S. PATENT DOCUMENTS

| 4,367,738 A | 1/1983 | Legendre et al. |
| 4,735,618 A * | 4/1988 | Hagen ................. A61M 5/3275 604/110 |

(Continued)

FOREIGN PATENT DOCUMENTS

| EP | 2878319 | 6/2015 |
| JP | 2013-529986 | 7/2013 |

(Continued)

OTHER PUBLICATIONS

International Preliminary Report on Patentability in International Application No. PCT/EP2017/067508, dated Jan. 15, 2019, 6 pages.
(Continued)

*Primary Examiner* — Emily L Schmidt
(74) *Attorney, Agent, or Firm* — Fish & Richardson P.C.

(57) ABSTRACT

The present disclosure relates to a body arrangement for a drug delivery device, comprising at least one deployable body part arranged to be moved from a compact state into a deployed state, wherein the body part in the deployed state provides an enlarged grip area compared to the compact state.

16 Claims, 8 Drawing Sheets

(52) U.S. Cl.
CPC ........ *A61M 5/3243* (2013.01); *A61M 5/3245* (2013.01); *A61M 5/3271* (2013.01); *A61M 5/3272* (2013.01); *A61M 5/3275* (2013.01); *A61M 5/5086* (2013.01); *A61M 2205/19* (2013.01); *A61M 2205/583* (2013.01); *A61M 2205/586* (2013.01)

(56) References Cited

U.S. PATENT DOCUMENTS

| | | | | |
|---|---|---|---|---|
| 4,898,589 | A | * | 2/1990 | Dolgin ................ A61M 5/322 604/110 |
| 5,487,733 | A | * | 1/1996 | Caizza ............... A61M 5/3275 604/110 |
| 5,695,474 | A | * | 12/1997 | Daugherty ......... A61M 5/3243 604/162 |
| 6,409,706 | B1 | * | 6/2002 | Loy .................... A61M 5/3275 604/110 |
| 2004/0044318 | A1 | * | 3/2004 | Fiser .................. A61M 5/3275 604/263 |
| 2006/0069347 | A1 | | 3/2006 | Besing |
| 2013/0030376 | A1 | * | 1/2013 | Doyle ................ A61M 5/3275 604/198 |
| 2014/0213983 | A1 | * | 7/2014 | Ekman ................ A61M 5/326 604/198 |

FOREIGN PATENT DOCUMENTS

| | | |
|---|---|---|
| JP | 2014-522707 | 9/2014 |
| JP | 2014-526292 | 10/2014 |
| JP | 2015-047478 | 3/2015 |
| WO | WO 2012/000833 | 1/2012 |
| WO | WO 2013/016365 | 1/2013 |
| WO | WO 2013/037743 | 3/2013 |

OTHER PUBLICATIONS

International Search Report and Written Opinion in International Application No. PCT/EP2017/067508, dated Oct. 10, 2017, 8 pages.

* cited by examiner

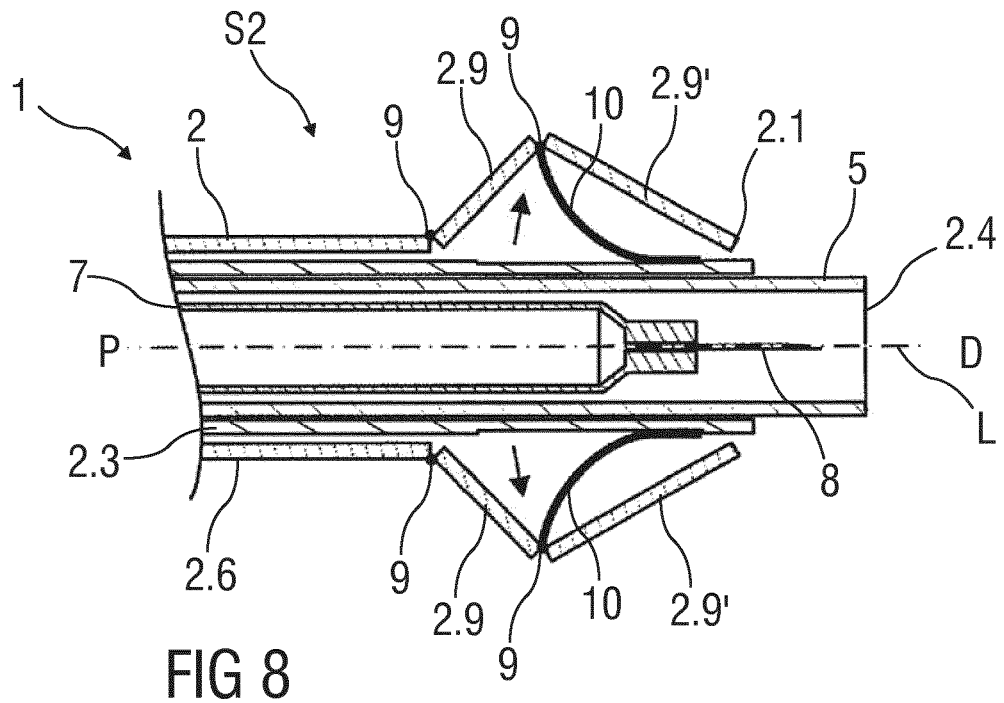
FIG 8
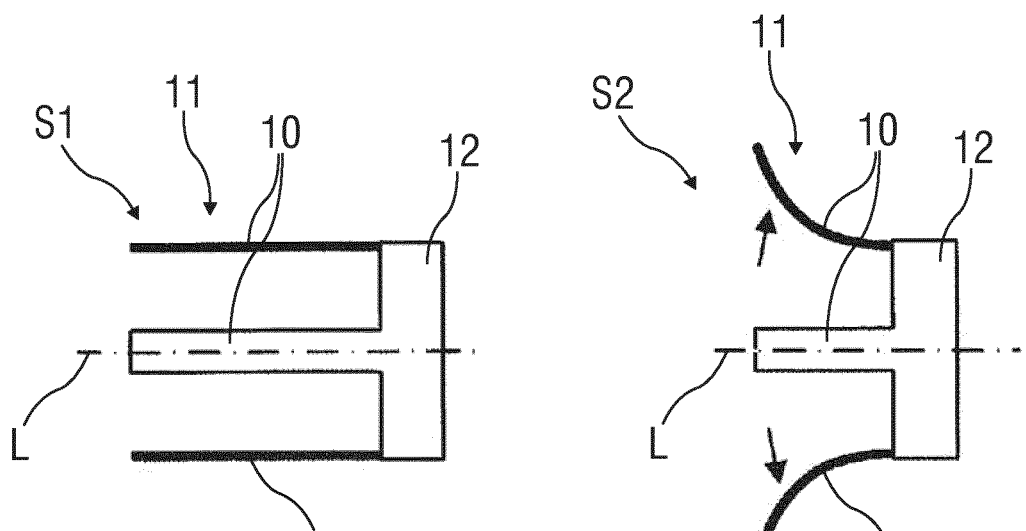
FIG 9
FIG 10

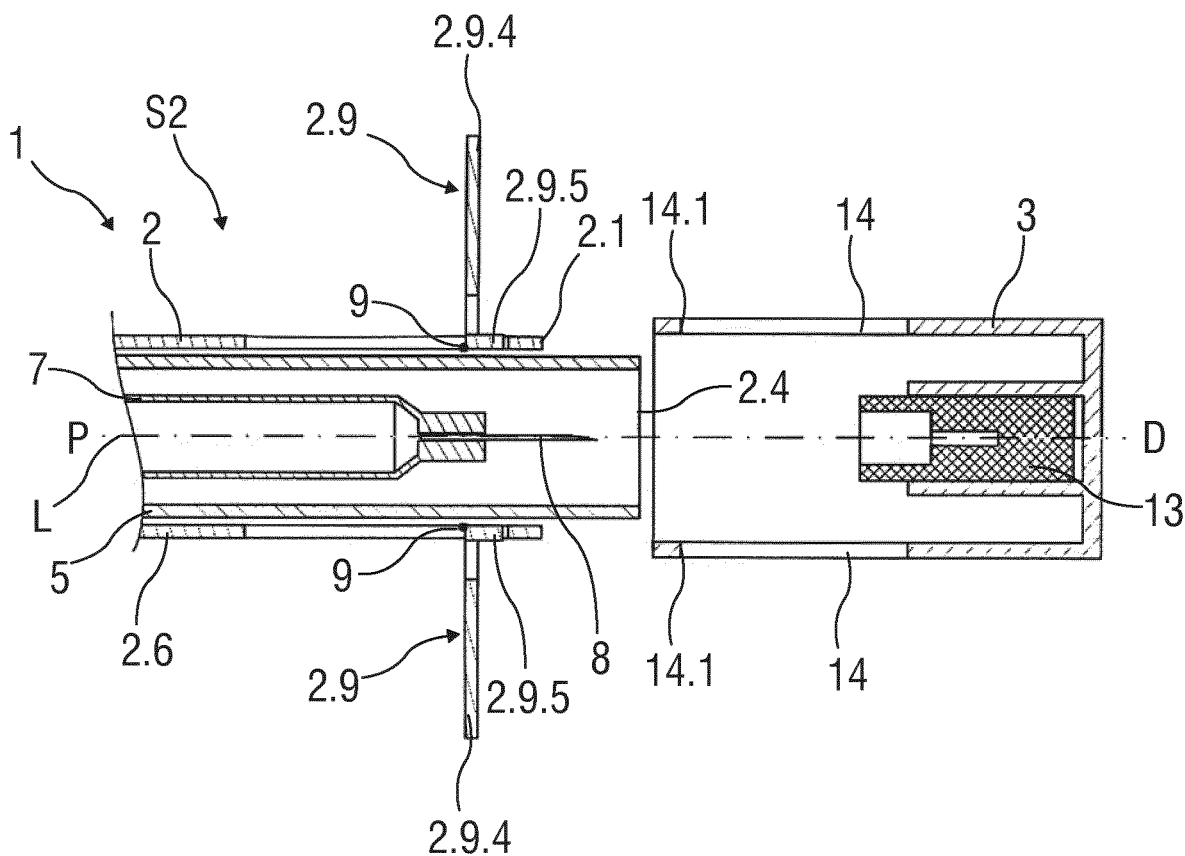
FIG 13
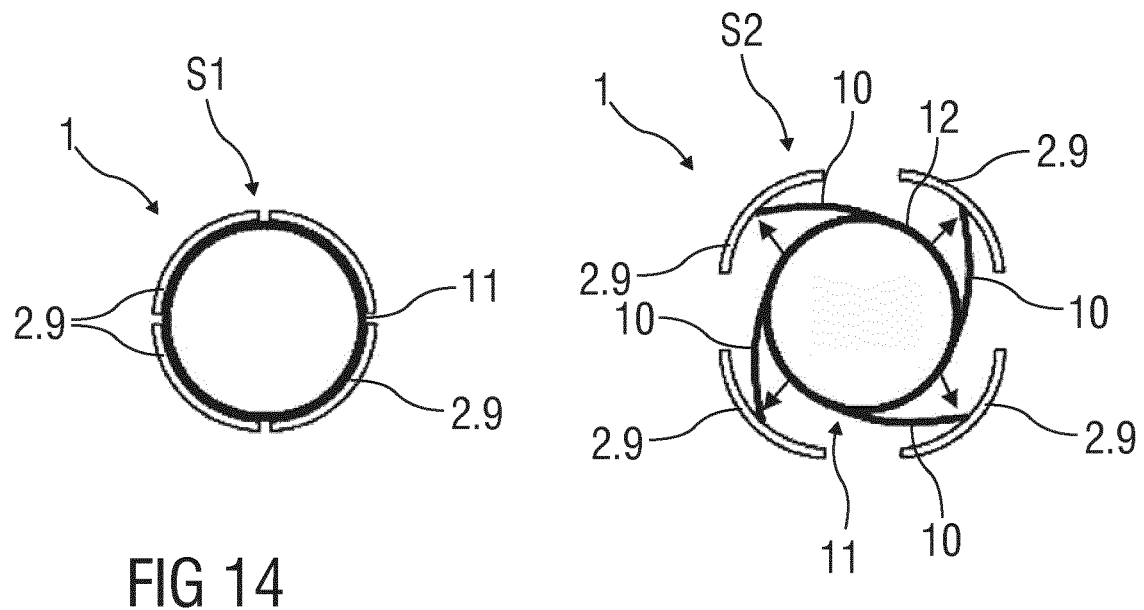
FIG 14
FIG 15

BODY ARRANGEMENT FOR A DRUG DELIVERY DEVICE

CROSS REFERENCE TO RELATED APPLICATIONS

The present application is the national stage entry of International Patent Application No. PCT/EP2017/067508, filed on Jul. 12, 2017, and claims priority to Application No. EP 16179489.6, filed on Jul. 14, 2016, the disclosures of which are incorporated herein by reference.

TECHNICAL FIELD

The present disclosure generally relates to a body arrangement for a drug delivery device.

BACKGROUND

Administering an injection is a process which presents a number of risks and challenges for users and healthcare professionals, both mental and physical. Pre-filled syringes containing a selected dosage of a medicament for administering the medicament to a patient are known in the art.

There remains a need for an improved body arrangement for a drug delivery device.

SUMMARY

In some embodiments of the present disclosure, an improved body arrangement for a drug delivery device is provided.

According to the present disclosure, a body arrangement for a drug delivery device comprises at least one deployable body part arranged to be moved from a compact state into a deployed state, wherein the body part in the deployed state provides an enlarged grip area compared to the compact state. This improves the handling of the drug delivery device and a visual indicator allowing recognizing that the drug delivery device has been used.

In an exemplary embodiment the deployable body part is a tubular inner deployable body part telescoped within a tubular outer body part, wherein in the compact state, most of the deployable body part is hidden within the outer body part, wherein the deployable body part is adapted to be partially pulled out of the outer body part in order to arrive in the deployed state.

In an exemplary embodiment the deployable body part comprises a grip feature extending from the outer body part both in the compact state and in the deployed state. A user may thus grip the deployable body part to pull it out. The grip feature may have the form of an eye wide enough to allow a user inserting a finger. Likewise, the grip feature may have other ergonomic forms.

In an exemplary embodiment the at least one deployable body part is foldable or rotatable, wherein at least one of the deployable body parts is attached at an end of a sleeve-shaped body part by at least one hinge, wherein in the compact state, the deployable body parts or main beams of the deployable body parts are flush or substantially flush with the sleeve-shaped body part, wherein at least one of the deployable body parts or a main beam thereof is adapted to be tilted or rotated about the at least one hinge away from a longitudinal axis in the deployed state.

In an exemplary embodiment further hinges are provided between at least two of the deployable body parts.

In an exemplary embodiment at least one further deployable body part is connected to an end of one of the deployable body parts by one of the hinges such that these further deployable body part is adapted to be tilted towards the longitudinal axis relative to the deployable body part.

In an exemplary embodiment the at least one deployable body part furthermore comprises a protrusion arranged at an angle with the main beam, wherein in the compact state, the protrusion points substantially radially outwards, wherein a cap is arrangeable over the main beam, the cap comprising at least one longitudinal slot adapted to receive the radially outwardly pointing protrusion, wherein a stop limits the longitudinal slots proximally such that the stop engages the protrusion when the cap is being removed in a distal direction. The deployable body part is thus automatically deployed upon removal of the cap.

In an exemplary embodiment the hinges are arranged as live hinges.

In an exemplary embodiment the deployable body part comprises a distal ring and a proximal ring and a plurality of slats extending from the distal ring to the proximal ring, wherein each of the slats at least comprises a helical section, wherein in the compact state, the slats are flush with the rings, wherein the rings are adapted to be rotated relative to one another and/or moved axially relative towards each other to deploy the slats outward in the deployed state.

In an exemplary embodiment the deployable body part is telescoped over an inner body part, wherein at least one of the rings is engaged to a guide on the inner body part, wherein the guide at least comprises an angled section which is angled with respect to a longitudinal direction.

In an exemplary embodiment the guide furthermore comprises a transversal section adapted to lock the at least one of the rings in position in the deployed state.

In an exemplary embodiment at least one spring is arranged to bias the at least one deployable body part towards the deployed state.

In an exemplary embodiment the at least one spring is a leaf spring adapted to be curved in a relaxed state.

In an exemplary embodiment two nested springs in the form of leaf springs are arranged, the springs being curved and having a first radius in a relaxed state, wherein in a pre-stressed state the springs have a second radius which is smaller than the first radius.

In an exemplary embodiment a button is arranged to release the spring.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein:

FIG. 8 is a schematic view of the body arrangement in a deployed state, FIG. 9 is a schematic view of a spring for deploying a body part of the body arrangement, wherein the spring is in a pre-stressed state, FIG. 10 is a schematic view of the spring in a relaxed state, FIG. 13 is a schematic view of the body arrangement in a deployed state, FIG. 14 is a schematic detail view of a sixth exemplary embodiment of a body arrangement in a compact state, FIG. 15 is a schematic view of the body arrangement in a deployed state.

Corresponding parts are marked with the same reference symbols in all figures.

DETAILED DESCRIPTION

Figure 1:
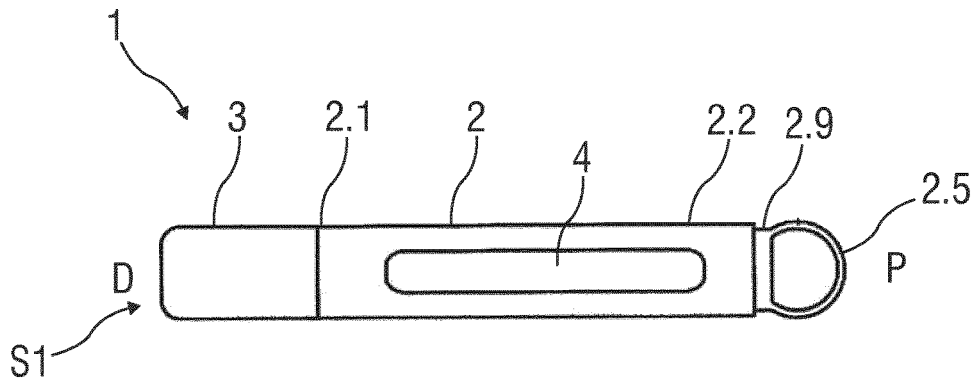
FIG. 1 is a schematic view of a first exemplary embodiment of a body arrangement in a compact state.
Figure 2:
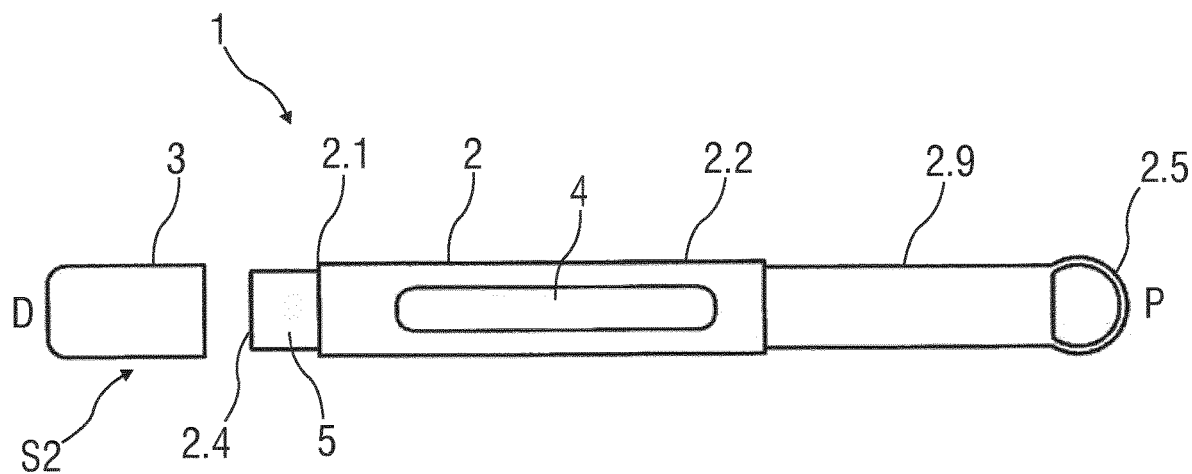
FIG. 2 is a schematic view of the body arrangement in a deployed state.

FIG. 1 is a schematic view of a first exemplary embodiment of a body arrangement 1 of a drug delivery device in a compact state S1. FIG. 2 is a schematic view of the body arrangement 1 in a deployed state S2. The body arrangement 1 comprises a body 2 and a cap 3 attached to a distal end 2.1 of the body 2. The body 2 may be adapted to retain a medicament cartridge to which an injection needle may be attached or a medicament cartridge in the form of a pre-filled syringe with an attached injection needle, which may extend from or be extended through an opening 2.4 in the distal end 2.1. The cap 3 is adapted to cover the opening 2.4 in the distal end 2.1 of the body 2 to prevent access to the injection needle. Furthermore, the cap 3 may be adapted to engage a protective needle sheath arranged over the injection needle in order to remove the protective needle sheath upon removal of the cap 3 from the distal end 2.1. The body 2 may comprise a viewing window 4 allowing inspection of the contents of the medicament cartridge or syringe. An activation mechanism may be arranged within the body 2, the activation mechanism adapted to advance the syringe and needle and/or to advance a stopper within the syringe for displacing a drug contained in the syringe through the injection needle. In an exemplary embodiment, a sleeve 5 is telescoped within the distal end 2.1 of the body 2, wherein the sleeve 5 may be adapted to be moved in a proximal direction P into the body 2 in order to expose the injection needle and/or to actuate the drug delivery device and/or to allow actuation of the activation mechanism.

The body 2 comprises a tubular outer body part 2.2 and a tubular inner deployable body part 2.9 telescoped within the outer body part 2.2. In the compact state S1, most of the deployable body part 2.9 is hidden within the outer body part 2.2. The deployable body part 2.9 may be partially pulled out of the outer body part 2.2 from the compact state S1 in a proximal direction P in order to arrive in the deployed state S2. The deployable body part 2.9 may comprise a grip feature 2.5 at a proximal end which extends from the outer body part 2.2 both in the compact state S1 and in the deployed state S2 such that a user may grip the deployable body part 2.9 to pull it out. The grip feature 2.5 may have the form of an eye wide enough to allow a user inserting a finger. Likewise, the grip feature 2.5 may have other ergonomic forms.

The body arrangement 1 in the deployed state S2 provides an enlarged grip area which improves the handling of the drug delivery device and a visual indicator allowing recognizing that the drug delivery device has been used. A stop may be provided to prevent the deployable body part 2.9 from being completely pulled out of the outer body part 2.2. A non-return feature, e.g. a clip or force fit, may be provided between the deployable body part 2.9 and the outer body part 2.2 preventing the deployable body part 2.9 from being moved out of the deployed state S2 back in the distal direction D. This allows for recognizing that the drug delivery device has been used and preventing the user from attempting reusing it. Movement of the deployable body part 2.9 out of the compact state S1 towards the deployed state S2 may be restricted by a detent or frictional engagement to the outer body part 2.2. In an exemplary embodiment, the deployable body part 2.9 may be engaged to the outer body part 2.2 by a bayonet requiring that the deployable body part 2.9 be first rotated by a defined angle relative to the outer body part 2.2 when in the compact state S1 before it can be pulled in the proximal direction D towards the deployed state S2.

Figure 3:
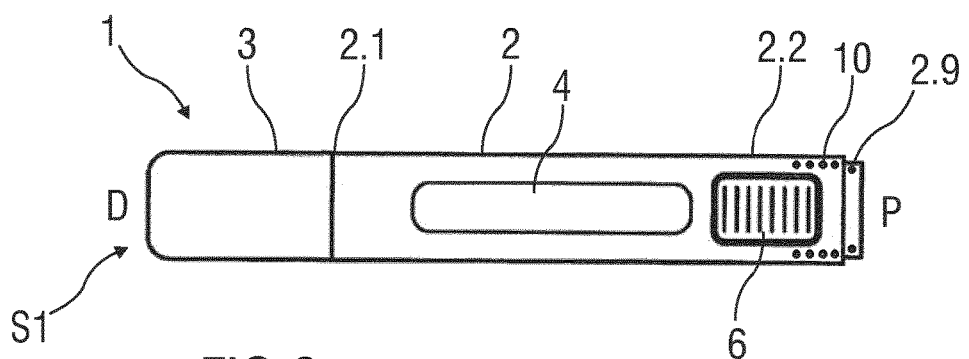
FIG. 3 is a schematic view of a second exemplary embodiment of a body arrangement in a compact state.
Figure 4:
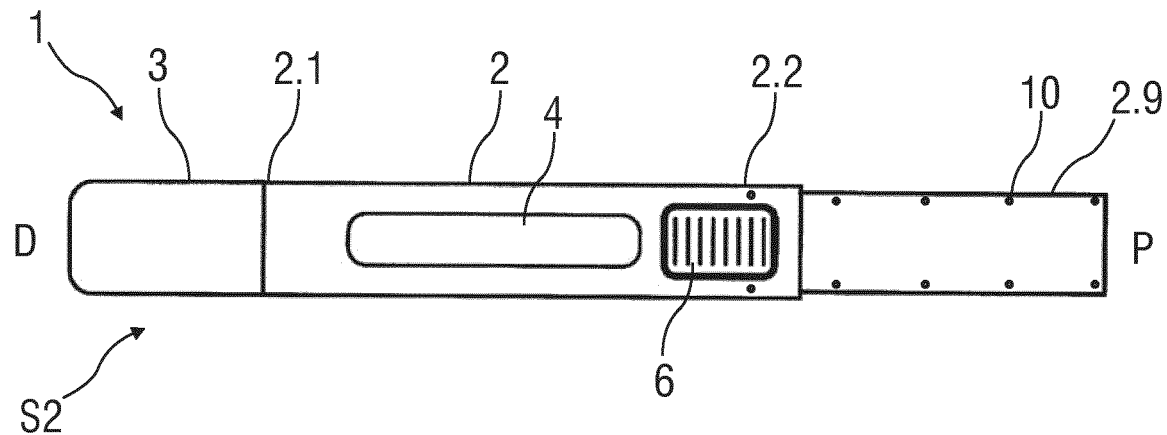
FIG. 4 is a schematic view of the body arrangement in a deployed state.

FIG. 3 is a schematic view of a second exemplary embodiment of a body arrangement 1 for a drug delivery device in a compact state S1. FIG. 4 is a schematic view of the body arrangement 1 in a deployed state S2. The body arrangement 1 comprises a body 2 and a cap 3 attached to a distal end 2.1 of the body 2. The body 2 may be adapted to retain a medicament cartridge to which an injection needle may be attached or a medicament cartridge in the form of a pre-filled syringe with an attached injection needle, which may extend from or be extended through an opening 2.4 in the distal end 2.1. The cap 3 is adapted to cover the opening 2.4 in the distal end 2.1 of the body 2 to prevent access to the injection needle. Furthermore, the cap 3 may be adapted to engage a protective needle sheath arranged over the injection needle in order to remove the protective needle sheath upon removal of the cap 3 from the distal end 2.1. The body 2 may comprise a viewing window 4 allowing inspection of the contents of the medicament cartridge or syringe. An activation mechanism may be arranged within the body 2, the activation mechanism adapted to advance the syringe and needle and/or to advance a stopper within the syringe for displacing a drug contained in the syringe through the injection needle. In an exemplary embodiment, a sleeve 5 is telescoped within the distal end 2.1 of the body 2, wherein the sleeve 5 may be adapted to be moved in a proximal direction P in order to expose the injection needle and/or to actuate the drug delivery device and/or to allow actuation of the activation mechanism.

The body 2 comprises a tubular outer body part 2.2 and a tubular inner deployable body part 2.9 telescoped within the outer body part 2.2. In the compact state S1, most of the deployable body part 2.9 is hidden within the outer body part 2.2. The deployable body part 2.9 may be partially moved out of the outer body part 2.2 from the compact state S1 in a proximal direction P in order to arrive in the deployed state S2. Movement of the deployable body part 2.9 out of the compact state S1 towards the deployed state S2 may be restricted by a locking mechanism. A spring 10 may be arranged to bias the deployable body part 2.9 in the proximal direction P relative to the outer body part 2.2. In the compact state S1, the spring 10 is prevented from relaxing and moving the deployable body part 2.9 in the proximal direction P by the locking mechanism. A button 6 is arranged to release the locking mechanism or the spring 10 allowing the spring 10 to move the deployable body part 2.9 in the proximal direction P out of the compact state S1 into the deployed state S2.

The body arrangement 1 in the deployed state S2 provides an enlarged grip area which improves the handling of the drug delivery device and a visual indicator allowing recognizing that the drug delivery device has been used. A stop may be provided to prevent the deployable body part 2.9 from being completely pulled out of the outer body part 2.2. A non-return feature, e.g. a clip or force fit, may be provided between the deployable body part 2.9 and the outer body part 2.2 preventing the deployable body part 2.9 from being moved out of the deployed state S2 back in the distal direction D. This allows for recognizing that the drug delivery device has been used and preventing the user from attempting reusing it.

Figure 5:
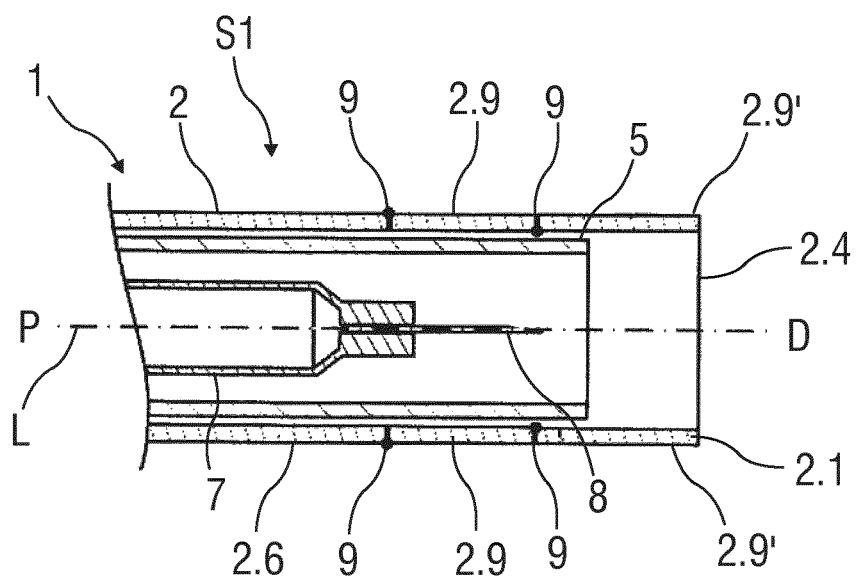
FIG. 5 is a schematic detail view of a third exemplary embodiment of a body arrangement in a compact state.
Figure 6:
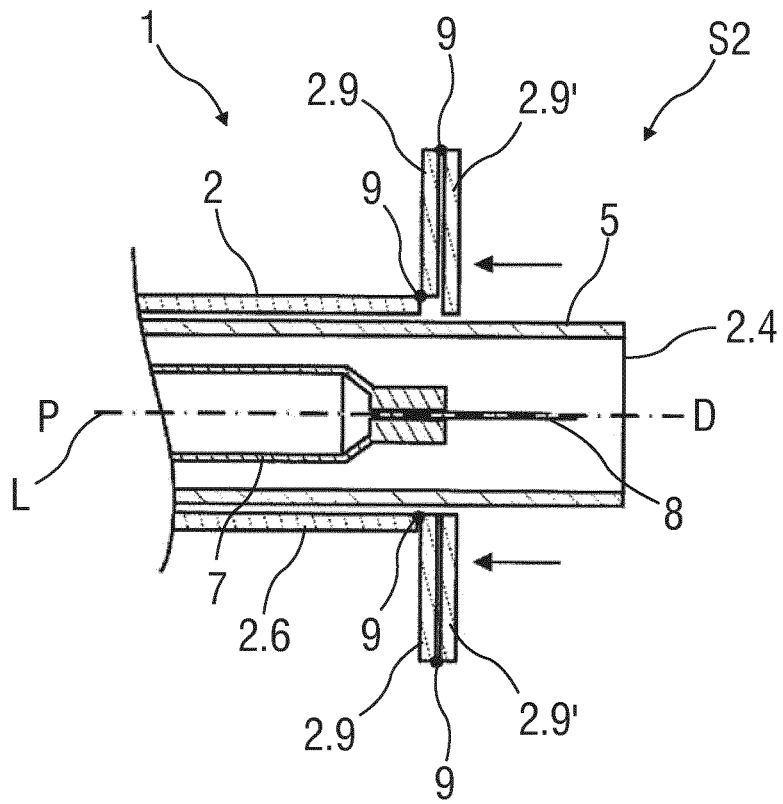
FIG. 6 is a schematic view of the body arrangement in a deployed state.

FIG. 5 is a schematic detail view of a third exemplary embodiment of a body arrangement 1 of a drug delivery device in a compact state S1. FIG. 6 is a schematic detail view of the body arrangement 1 in a deployed state S2. The body arrangement 1 comprises a body 2. A cap (not shown) may be attached to a distal end 2.1 of the body 2. The body 2 may be adapted to retain a medicament cartridge 7 to which an injection needle 8 may be attached. In the illustrated embodiment, the medicament cartridge 7 is a pre-filled syringe with an attached injection needle 8, which may extend from or be extended through an opening 2.4 in the distal end 2.1. The cap may be adapted to cover the opening 2.4 in the distal end 2.1 of the body 2 to prevent access to the injection needle 8. Furthermore, the cap may be adapted to engage a protective needle sheath arranged over the injection needle in order to remove the protective needle sheath upon removal of the cap from the distal end 2.1. The body 2 may comprise a viewing window (not illustrated) allowing inspection of the contents of the medicament cartridge 7. An activation mechanism may be arranged within the body 2, the activation mechanism adapted to advance the medicament cartridge 7 and needle 8 and/or to advance a stopper within the medicament cartridge 7 for displacing a drug contained in the medicament cartridge 7 through the injection needle 8. In an exemplary embodiment, a sleeve 5 is telescoped within the distal end 2.1 of the body 2, wherein the sleeve 5 may be adapted to be moved in a proximal direction P into the body 2 in order to expose the injection needle 8 and/or to actuate the drug delivery device and/or to allow actuation of the activation mechanism.

The body 2 comprises a sleeve-shaped body part 2.6 and one or more foldable deployable body parts 2.9, 2.9' at least some of them attached at a distal end of the sleeve-shaped body part 2.6 by one or more hinges 9. Further hinges 9 may be provided between at least two of the deployable body parts 2.9, 2.9'. The hinges 9 may be arranged as live hinges. In the compact state S1, the deployable body parts 2.9, 2.9' are flush or substantially flush with the sleeve-shaped body part 2.6, i.e. aligned with the sleeve-shaped body part 2.6 in parallel to a longitudinal axis L of the body arrangement 1. The illustrated embodiment shows two deployable body parts 2.9 connected to the sleeve-shaped body part 2.6 by respective hinges 9 such that these deployable body parts 2.9 may be tilted away from the longitudinal axis L in the deployed state S2. Two further deployable body parts 2.9' are respectively connected to distal ends of the other deployable body parts 2.9 by respective hinges 9 such that these further deployable body parts 2.9' may be tilted towards the longitudinal axis L relative to the other deployable body parts 2.9.

The body arrangement 1 in the deployed state S2 provides an enlarged grip area which improves the handling of the drug delivery device, e.g. by serving as a stop for a user's hand to keep it from slipping all the way to the distal end 2.1. Furthermore, the deployed state S2 provides a visual indicator allowing recognizing that the drug delivery device has been used. The deployable body parts 2.9, 2.9' in the deployed state S2 may also prevent a user from re-attaching a cap over the body 2 thus providing a further indication that the drug delivery device has been used and preventing reuse. The folding of the deployable body parts 2.9, 2.9' may be achieved by sliding of the cap or another part which is connected to the deployable body parts 2.9, 2.9'. A spring 10 may be provided to automatically fold the deployable body parts 2.9, 2.9' after activation which may be performed e.g. by pressing a button 6 or turning the cap. One or more non-return features, e.g. clips, may be provided for locking the deployable body parts 2.9, 2.9' in the deployed state S2.

Figure 7:
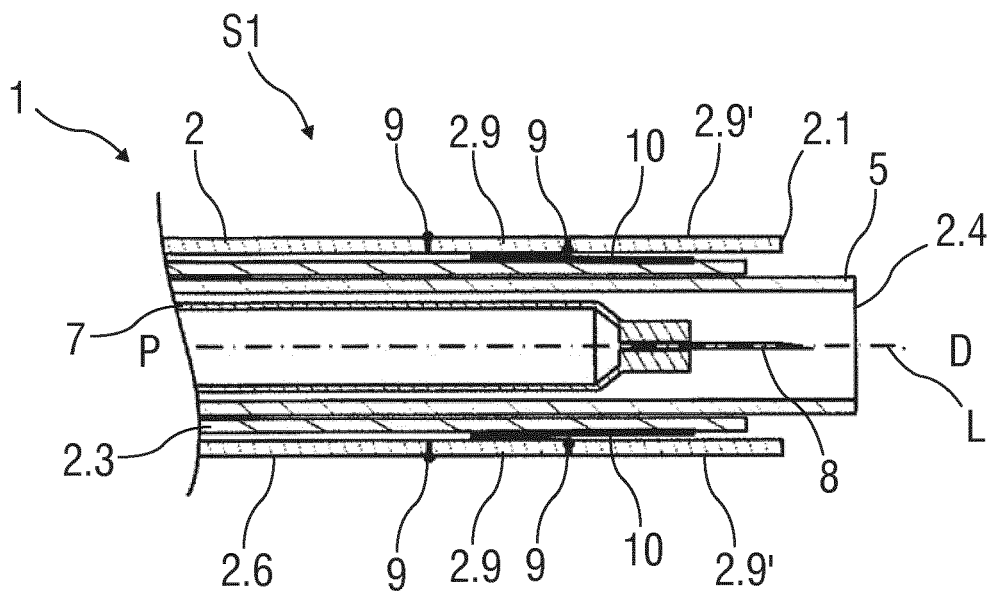
FIG. 7 is a schematic detail view of a fourth exemplary embodiment of a body arrangement in a compact state.

FIG. 7 is a schematic detail view of a fourth exemplary embodiment of a body arrangement 1 of a drug delivery device in a compact state S1. FIG. 8 is a schematic view of the body arrangement 1 in a deployed state S2. The body arrangement 1 comprises a body 2. A cap (not shown) may be attached to a distal end 2.1 of the body 2. The body 2 may be adapted to retain a medicament cartridge 7 to which an injection needle 8 may be attached. In the illustrated embodiment, the medicament cartridge 7 is a pre-filled syringe with an attached injection needle 8, which may extend from or be extended through an opening 2.4 in the distal end 2.1. The cap may be adapted to cover the opening 2.4 in the distal end 2.1 of the body 2 to prevent access to the injection needle 8. Furthermore, the cap may be adapted to engage a protective needle sheath arranged over the injection needle 8 in order to remove the protective needle sheath upon removal of the cap from the distal end 2.1. The body 2 may comprise a viewing window (not illustrated) allowing inspection of the contents of the medicament cartridge 7. An activation mechanism may be arranged within the body 2, the activation mechanism adapted to advance the medicament cartridge 7 and injection needle 8 and/or to advance a stopper within the medicament cartridge 7 for displacing a drug contained in the medicament cartridge 7 through the injection needle 8. In an exemplary embodiment, a sleeve 5 is telescoped within the distal end 2.1 of the body 2, wherein the sleeve 5 may be adapted to be moved in a proximal direction P into the body 2 in order to expose the injection needle 8 and/or to actuate the drug delivery device and/or to allow actuation of the activation mechanism.

The body 2 comprises a sleeve-shaped body part 2.6 and one or more foldable deployable body parts 2.9, 2.9' at least some of them attached at a distal end of the sleeve-shaped body part 2.6 by one or more hinges 9. Further hinges 9 may be provided between at least two of the deployable body parts 2.9, 2.9'. The hinges 9 may be arranged as live hinges. In the compact state S1, the deployable body parts 2.9, 2.9' are flush or substantially flush with the sleeve-shaped body part 2.6, i.e. aligned with the sleeve-shaped body part 2.6 in parallel to a longitudinal axis L of the body arrangement 1. The illustrated embodiment shows two deployable body parts 2.9 connected to the sleeve-shaped body part 2.6 by respective hinges 9 such that these deployable body parts 2.9 may be tilted away from the longitudinal axis L. Two further deployable body parts 2.9' are respectively connected to distal ends of the other deployable body parts 2.9 by respective hinges 9 such that these further deployable body parts 2.9' may be tilted towards the longitudinal axis L relative to the other deployable body parts 2.9. One or more springs 10 are provided to automatically fold the deployable body parts 2.9, 2.9' after activation which may be performed e.g. by removing the cap 3. An inner body part 2.3 is arranged within the outer sleeve shaped body part 2.6 and within the deployable body parts 2.9, 2.9'. The springs 10 may be leaf springs supported at one end on the inner body part 2.3 and arranged to be substantially straight when pre-stressed in the compact state S1. If the deployable body parts 2.9, 2.9' are allowed to move into the deployed state S2, e.g. by removing the cap 3, the springs 10 relax into a curved form and deploy the deployable body parts 2.9, 2.9'. In the deployed state S2, an end of each spring 10 which is not attached to the inner body part 2.3 may engage at one of the hinges 9 between one of the deployable body parts 2.9 and one of the deployable body parts 2.9'. One or more non-return features, e.g. clips, may be provided for locking the deployable body parts 2.9, 2.9' in the deployed state S2.

FIG. 9 is a schematic view of a spring arrangement 11 for deploying the deployable body parts 2.9, 2.9'. The spring arrangement 11 comprises a ring 12 which may be arranged about the inner body part 2.3 and one or more, e.g. four, springs 10 extending from the ring 12 in the proximal direction P. In an exemplary embodiment, the springs 10 may be integrally formed with the ring. The springs 10 and/or the ring 12 may consist of sheet metal. In FIG. 9, the springs 10 are in a pre-stressed state as in FIG. 7. In FIG. 10, the springs 10 are in a relaxed state as in FIG. 8.

The body arrangement 1 in the deployed state S2 provides an enlarged grip area which improves the handling of the drug delivery device, e.g. by serving as a stop for a user's hand to keep it from slipping all the way to the distal end 2.1. Furthermore, the deployed state S2 provides a visual indicator allowing recognizing that the drug delivery device has been used. The deployable body parts 2.9, 2.9' in the deployed state S2 may also prevent a user from re-attaching a cap 3 over the body 2 thus providing a further indication that the drug delivery device has been used and preventing reuse. The folding of the deployable body parts 2.9, 2.9' may be achieved by sliding of the cap 3 or another part which is connected to the deployable body parts 2.9, 2.9'.

Figure 11:
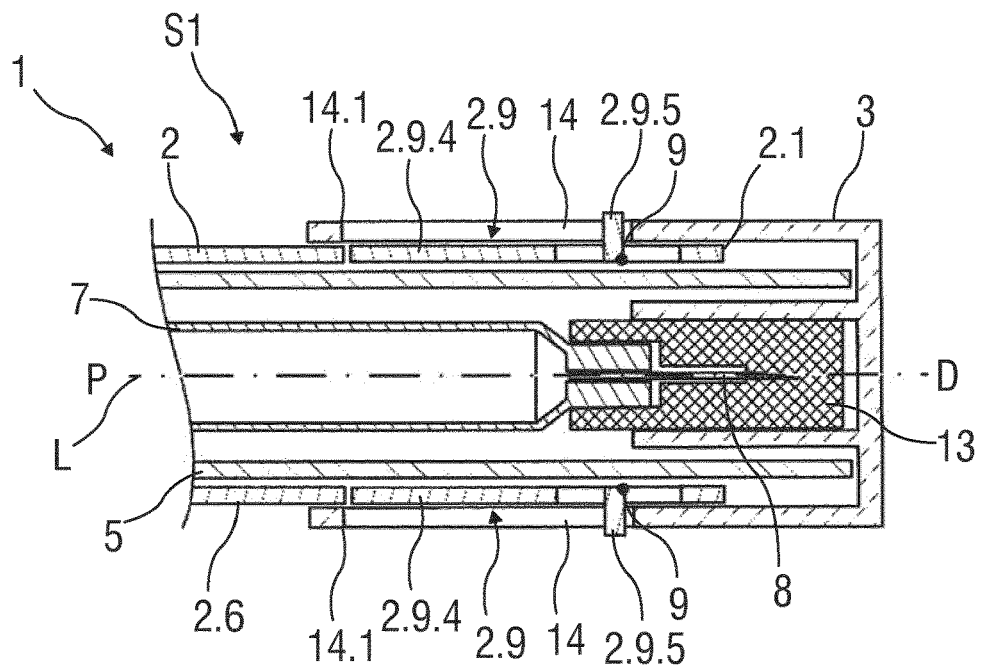
FIG. 11 is a schematic detail view of a fifth exemplary embodiment of a body arrangement in a compact state.
Figure 12:
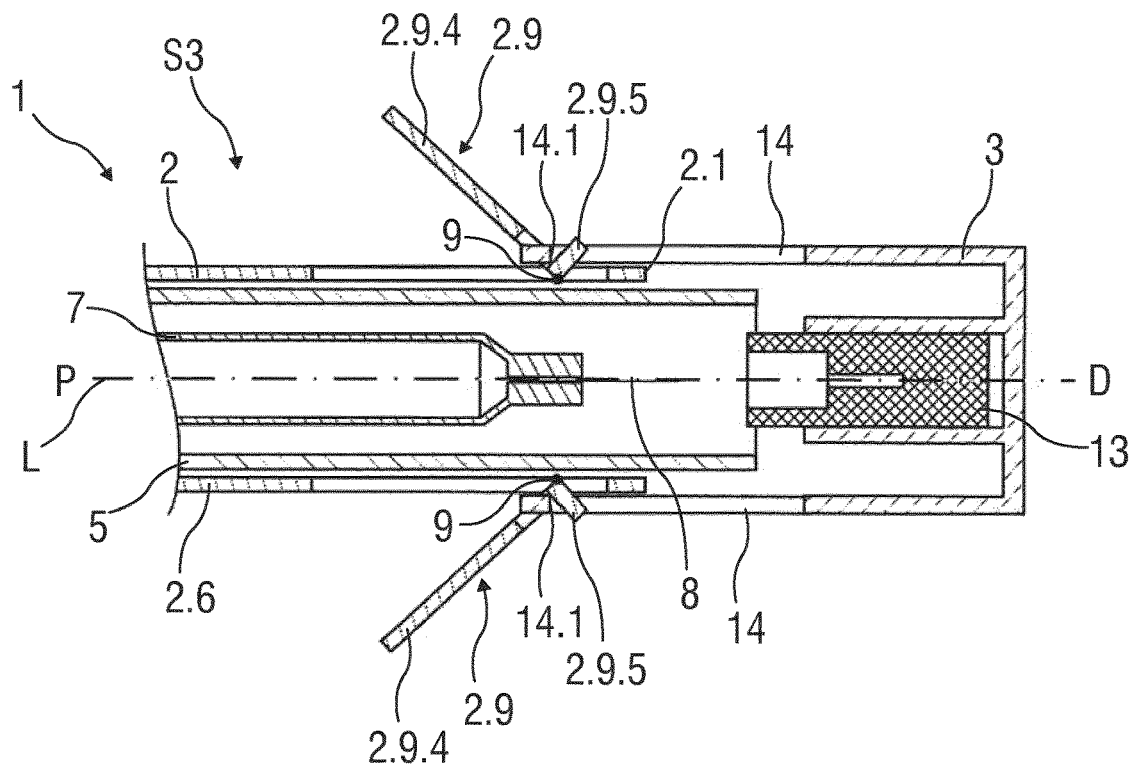
FIG. 12 is a schematic view of the body arrangement in an intermediate state.

FIG. 11 is a schematic detail view of a fifth exemplary embodiment of a body arrangement 1 of a drug delivery device in a compact state S1. FIG. 12 is a schematic view of the body arrangement 1 in an intermediate state S3. FIG. 13 is a schematic view of the body arrangement 1 in a deployed state S2. The body arrangement 1 comprises a body 2. A cap 3 may be attached to a distal end 2.1 of the body 2. The body 2 may be adapted to retain a medicament cartridge 7 to which an injection needle 8 may be attached. In the illustrated embodiment, the medicament cartridge 7 is a pre-filled syringe with an attached injection needle 8, which may extend from or be extended through an opening 2.4 in the distal end 2.1. The cap 3 may be adapted to cover the opening 2.4 in the distal end 2.1 of the body 2 to prevent access to the injection needle 8. Furthermore, the cap 3 may be adapted to engage a protective needle sheath 13 arranged over the injection needle 8 in order to remove the protective needle sheath 13 upon removal of the cap 3 from the distal end 2.1. The body 2 may comprise a viewing window (not illustrated) allowing inspection of the contents of the medicament cartridge 7. An activation mechanism may be arranged within the body 2, the activation mechanism adapted to advance the medicament cartridge 7 and needle 8 and/or to advance a stopper within the medicament cartridge 7 for displacing a drug contained in the medicament cartridge 7 through the injection needle 8. In an exemplary embodiment, a sleeve 5 is telescoped within the distal end 2.1 of the body 2, wherein the sleeve 5 may be adapted to be moved in a proximal direction P into the body 2 in order to expose the injection needle 8 and/or to actuate the drug delivery device and/or to allow actuation of the activation mechanism.

The body 2 comprises a sleeve-shaped body part 2.6 and one or more rotatable deployable body parts 2.9 attached at a distal end of the sleeve-shaped body part 2.6 by one or more hinges 9 such that a rotational axis of the hinges 9 is tangential with respect to the longitudinal axis L. The deployable body parts 2.9 respectively comprise a main beam 2.9.4 and a protrusion 2.9.5 arranged at an angle, e.g. at right angles, with the main beam 2.9.4. At an intersection of the main beam 2.9.4 with the protrusion 2.9.5, the deployable body part 2.9 is attached to the hinge 9. In the compact state S1, the main beams 2.9.4 of the deployable body parts 2.9 are flush or substantially flush with the sleeve-shaped body part 2.6, i.e. aligned with the sleeve-shaped body part 2.6 in parallel to the longitudinal axis L of the body arrangement 1 and the protrusions 2.9.5 point substantially radially outwards. The cap 3 is initially arranged over the sleeve 5 and the main beams 2.9.4 of the deployable body parts 2.9 and may extend over a section of the sleeve-shaped body part 2.6 proximally from the deployable body parts 2.9. The cap 3 comprises longitudinal slots 14 adapted to receive the radially outwardly pointing protrusions 2.9.5. A respective stop 14.1 limits each longitudinal slots 14 proximally such that the stop 14.1 engages the protrusion 2.9.5 received in the slot 14 when the cap 3 is being removed from the distal end 2.1 in the distal direction D. In FIG. 11, the body arrangement 1 is in the compact state S1, the main beams 2.9.4 of the deployable body parts 2.9 are flush or substantially flush with the sleeve-shaped body part 2.6, the protrusions 2.9.5 point substantially radially outwards and the cap 3 is arranged on the distal end 2.1. In FIG. 12, the body arrangement 1 is in an intermediate state S3, the cap 3 is being removed in the distal direction D from the distal end 2.1, the cap 3 takes the protective needle sheath 13 with it and removes it from the needle 8, the stops 14.1 engage the protrusions 2.9.5 and thus rotate the main beams 2.9.4 outwards about the hinges 9. In FIG. 13, the body arrangement 1 is in the deployed state S2, the cap 3 has been fully removed from the distal end 2.1. The stops 14.1 have thus rotated the deployable body parts 2.9 so that the protrusions 2.9.5 are now substantially flush with the sleeve-shaped body part 2.6 and the main beams 2.9.4 hence protrude radially outwards.

The body arrangement 1 in the deployed state S2 provides an enlarged grip area which improves the handling of the drug delivery device, e.g. by serving as a stop for a user's hand to keep it from slipping all the way to the distal end 2.1. Furthermore, the deployed state S2 provides a visual indicator allowing recognizing that the drug delivery device has been used. The deployable body parts 2.9 in the deployed state S2 may also prevent a user from re-attaching the cap 3 over the body 2 thus providing a further indication that the drug delivery device has been used and preventing reuse. In modified embodiments, the deployable body parts 2.9 may be rotated by pushing a button 6 or removing the drug delivery device out of a packaging. A clip or latch comprising one or more parts may be arranged on the body 2 for locking the deployable body parts 2.9 in the deployed state S2.

FIG. 14 is a schematic detail front view of a sixth exemplary embodiment of a body arrangement 1 of a drug delivery device in a compact state S1. FIG. 15 is a schematic view of the body arrangement 1 in a deployed state S2. The body arrangement 1 may be similar to one of the embodiments of FIGS. 5 to 13 comprising a body 2 with a sleeve-shaped body part (not shown). The body 2 comprises a number of deployable body parts 2.9 which may be deflectable, deployable or rotatable. In the illustrated embodiment, four deployable body parts 2.9 are provided. A spring arrangement 11 comprising a ring 12 and a number of springs 10 in the form of leaf springs are arranged to bias the deployable body parts 2.9 outwards. Each spring 10 is attached with one end to the ring 12. In the compact state S1, the deployable body parts 2.9 are flush or substantially flush with the sleeve-shaped body part 2.6, i.e. aligned with the sleeve-shaped body part in parallel to a longitudinal axis L of the body arrangement 1 and the springs 10 are pre-stressed such that they form circular sections of a circle. In the deployed state S2, the springs 10 are relaxed and tend to straighten such that an end of each spring 10 which is not connected to the ring 12 deflects one respective deployable body part 2.9 outwards. In an exemplary embodiment, the springs 10 may be integrally formed with the ring 12. The springs 10 and/or the ring 12 may consist of sheet metal.

Figure 16:
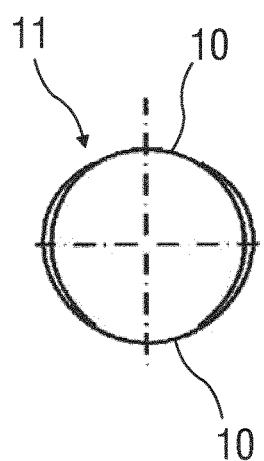
FIG. 16 is a schematic view of a spring arrangement for deploying body parts of a body arrangement in a pre-stressed state.
Figure 17:
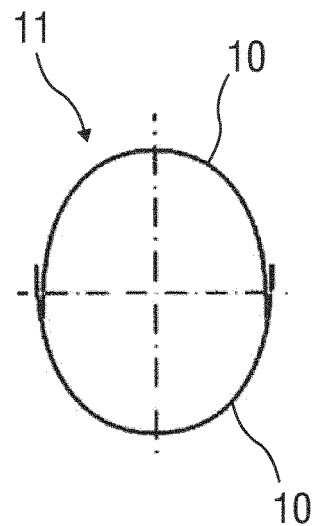
FIG. 17 is a schematic view of the spring arrangement in a relaxed state.

FIG. 16 is a schematic view of another embodiment of a spring arrangement 11 for deploying body parts of a body arrangement 1 in a pre-stressed state. FIG. 17 is a schematic view of the spring arrangement 11 in a relaxed state. The spring arrangement 11 comprises two springs 10 in the form of leaf springs. The springs 10 are curved and have a first radius in the relaxed state. The springs 10 are nested, i.e. one of the springs 10 is partially arranged within the other such that they enclose an at least nearly elliptical area. In the pre-stressed state the springs 10 are still nested and have a second radius which is smaller than the first radius such that they enclose an at least nearly circular area. The spring arrangement 11 may be applied with an embodiment of a body arrangement 1 as in one of the FIGS. 5 to 15.

In another exemplary embodiment, a spring arrangement 11 may comprise multiple springs 10 in the form of blades which rotate and fan out. The deployment of the deployable body parts 2.9 may comprise radial outward movement and/or axial movement, i.e. movement in the direction of the longitudinal axis L. The deployable body parts 2.9, 2.9' may be integral with the body 2 or may be separate parts which may be attached to the body 2 and can be disposable or reusable.

Figure 18:
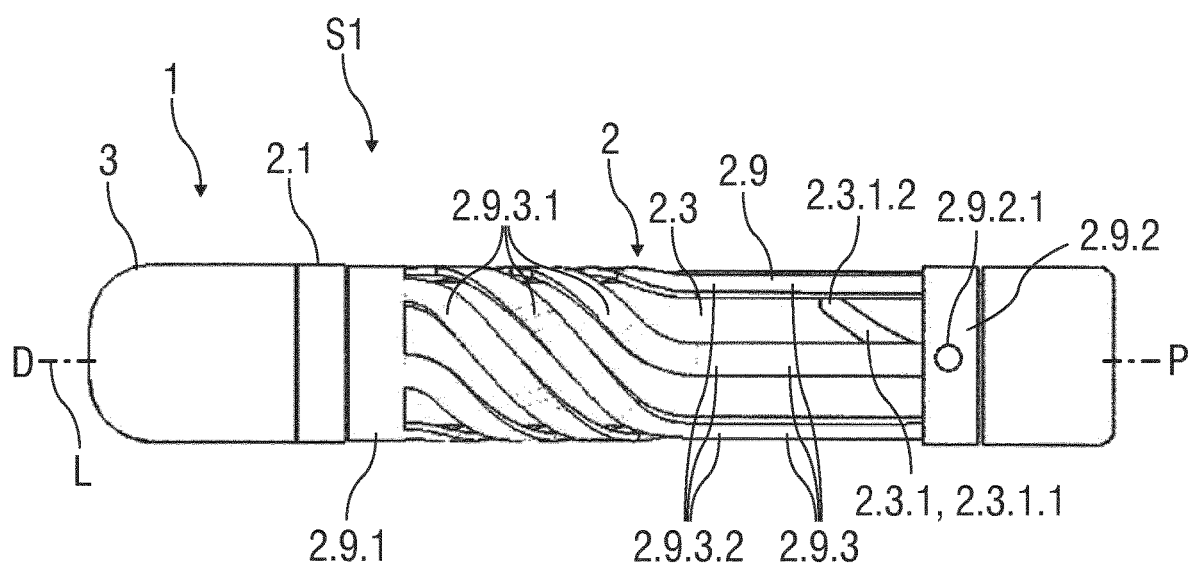
FIG. 18 is a schematic view of seventh exemplary embodiment of a body arrangement in a compact state.
Figure 19:
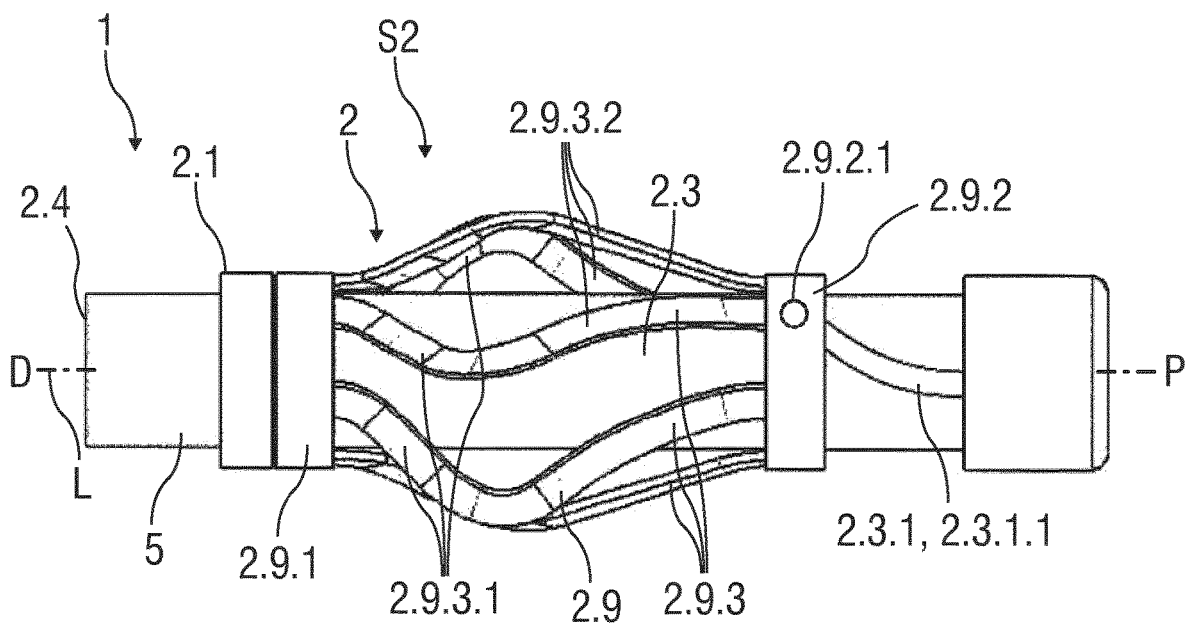
FIG. 19 is a schematic view of the body arrangement in a deployed state.

FIG. 18 is a schematic view of seventh exemplary embodiment of a body arrangement 1 of a drug delivery device in a compact state S1. FIG. 19 is a schematic view of the body arrangement 1 in a deployed state S2. The body arrangement 1 comprises a body 2 and a cap 3 attached to a distal end 2.1 of the body 2. The body 2 may be adapted to retain a medicament cartridge to which an injection needle may be attached or a medicament cartridge in the form of a pre-filled syringe with an attached injection needle, which may extend from or be extended through an opening 2.4 in the distal end 2.1. The cap 3 is adapted to cover the opening 2.4 in the distal end 2.1 of the body 2 to prevent access to the injection needle. Furthermore, the cap 3 may be adapted to engage a protective needle sheath arranged over the injection needle in order to remove the protective needle sheath upon removal of the cap 3 from the distal end 2.1. The body 2 may comprise a viewing window allowing inspection of the contents of the medicament cartridge or syringe. An activation mechanism may be arranged within the body 2, the activation mechanism adapted to advance the syringe and needle and/or to advance a stopper within the syringe for displacing a drug contained in the syringe through the injection needle. In an exemplary embodiment, a sleeve 5 is telescoped within the distal end 2.1 of the body 2, wherein the sleeve 5 may be adapted to be moved in a proximal direction P into the body 2 in order to expose the injection needle and/or to actuate the drug delivery device and/or to allow actuation of the activation mechanism.

The body 2 comprises an outer deployable body part 2.9 and an inner body part 2.3 telescoped within the deployable body part 2.9. The deployable body part 2.9 comprises a distal ring 2.9.1 and a proximal ring 2.9.2 and a plurality of slats 2.9.3 extending from the distal ring 2.9.1 to the proximal ring 2.9.2. In the compact state S1, each of the slats 2.9.3 at least comprises a helical section 2.9.3.1. In the illustrated embodiment, each slat 2.9.3 furthermore comprises a longitudinal section 2.9.3.2 in parallel with the longitudinal axis L of the body arrangement 1. In the compact state S1, the slats 2.9.3 are flush with the rings 2.9.1, 2.9.2 such that the deployable body part 2.9 is substantially sleeve-shaped. In the deployed state S2, the rings 2.9.1, 2.9.2 are rotated relative to one another in one rotational direction or moved axially relative towards each other. Hence, the slats 2.9.3 are deployed outward such that the deployable body part 2.9 is no longer sleeve-shaped.

The deployable body part 2.9 may be made from an elastic material, e.g. a thermoplastic elastomer or polypropylene or polyethylene or from sheet metal with a coating, e.g. rubber coating, which allows large displacements.

In an exemplary embodiment, the deployable body part 2.9 may be an additional part attachable to the inner body part 2.3. One of the rings 2.9.1, 2.9.2, e.g. the distal ring 2.9.1, may be fixed relative to the inner body part 2.3 and the other one of the rings, e.g. the proximal ring 2.9.2 may be engaged to a guide 2.3.1, e.g. by a protrusion 2.9.2.1 within the proximal ring 2.9.2 engaging a guide 2.3.1 in the form of a guide notch on or within the outer surface of the inner body part 2.3. The guide 2.3.1 at least comprises an angled section 2.3.1.1 which is angled with respect to the longitudinal direction, e.g. a helical section. In other, non-illustrated embodiments, the proximal ring 2.9.2 may be fixed and the distal ring 2.9.1 may be guided or both rings 2.9.1, 2.9.2 may be guided.

The deployable body part 2.9 may be moved from the compact state S1 to the deployed state S2 in different ways. In one embodiment the deployable body part 2.9 is deployed by pulling the cap 3. The cap 3 may be connected to the sleeve 5. By pulling the cap 3, the sleeve 5 is also pulled. The proximal ring 2.9.2 of the deployable body part 2.9 is connected to the sleeve 5 and engaged with the guide 2.3.1. When the sleeve 5 is pulled towards the distal end 2.1 of the body arrangement 1, the proximal ring 2.9.2 is also pulled in the distal direction D and consequently rotates and moves axially towards the distal ring 2.9.1 such that the slats 2.9.3 are deployed. The proximal ring 2.9.2 of the deployable body part 2.9 is then released from the sleeve 5 and is locked in position relative to the inner body part 2.3, e.g. by a transversal section 2.3.1.2 in the guide 2.3.1. The sleeve 5 then can move independently and the deployable body part 2.9 with the deployed slats 2.9.3 is fixed.

In an exemplary embodiment a trigger may be arranged to deploy the deployable body part 2.9 (e.g. by a spring). In another embodiment the deployable body part 2.9 may be manually compressed and/or rotated to deploy the slats 2.9.3.

It is also possible to integrate the spring effect in the deployable body part 2.9. In this case the deployable body part 2.9 may be produced unfolded, i.e. compressed with bent slats 2.9.3. During assembly, the deployable body part 2.9 is stretched, i.e. the proximal ring 2.9.2 is moved away from the distal ring 2.9.1. To freeze this stretched and cylindrical deployable body part 2.9, both rings 2.9.1, 2.9.2 are fixated during assembly and released before application to deploy the deployable body part 2.9. Another possibility to freeze the stretched deployable body part 2.9 and to release it is an outer sleeve, which may be part of a packaging, which needs to be removed before application, whereby the deployable body part 2.9 deploys itself. In an exemplary embodiment, the deployable body part 2.9 may be pre-tensioned in the compact state S1 and prevented from deploying by arranging a cap 3 over the deployable body part 2.9. After removal of the cap 3, the tension in the deployable body part 2.9 moves it into the deployed state S2.

The deployable body part 2.9 may be part of the drug delivery device or attachable by the user. The deployable body part 2.9 may be part of a drug delivery device with a single or a multiple use. In case of a multiple use, the deployable body part 2.9 may be restored to the compact state S1. In order to achieve this reverse movement, a bayonet joint can be integrated to fix and release the rings 2.9.1, 2.9.2.

The body arrangement 1 in the deployed state S2 provides an enlarged grip area which improves the handling of the drug delivery device and a visual indicator allowing recognizing that the drug delivery device has been used.

Figure 20:
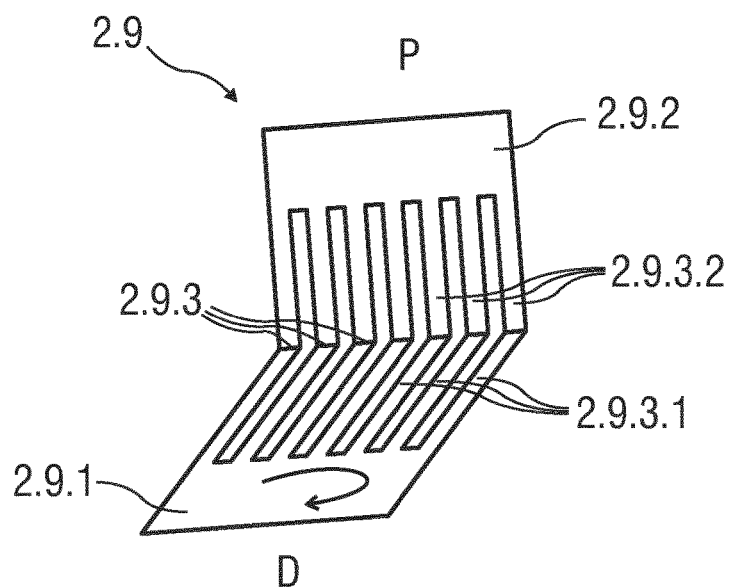
FIG. 20 is a schematic view of an exemplary embodiment of an outer body part during manufacturing.

FIG. 20 is a schematic view of an exemplary embodiment of the deployable body part 2.9 during manufacturing comprising a sheet material. The sheet material is cut to form the distal ring 2.9.1, the proximal ring 2.9.2 and the slats 2.9.3 with the helical sections 2.9.3.1 and the longitudinal sections 2.9.3.2. The distal ring 2.9.1 and the proximal ring 2.9.2 are respectively bent to form circular cylinders to arrive in the state as in FIG. 18 or FIG. 19.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 body arrangement
2 body
2.1 distal end
2.2 outer body part
2.3 inner body part
2.3.1 guide
2.3.1.1 angled section
2.3.1.2 transversal section
2.4 opening
2.5 grip feature
2.6 sleeve shaped body part
2.9 deployable body part
2.9.1 distal ring
2.9.2 proximal ring
2.9.2.1 protrusion
2.9.3 slat
2.9.3.1 helical section
2.9.3.2 longitudinal section
2.9.4 main beam
2.9.5 protrusion
2.9' deployable body part
3 cap
4 viewing window
5 sleeve
6 button
7 medicament cartridge
8 needle
9 hinge
10 spring
11 spring arrangement
12 ring
13 protective needle sheath
14 longitudinal slot
14.1 stop
D distal direction
L longitudinal axis
P proximal direction
S1 compact state
S2 deployed state
S3 intermediate state

The invention claimed is:

1. A drug delivery device, comprising:
a body arrangement adapted to retain a medicament container with an injection needle, the body arrangement comprising at least two deployable body parts arranged to be moved from a compact state into a deployed state, wherein the at least two deployable body parts in the deployed state provide an enlarged grip area compared to the compact state, and
a sleeve at least partially disposed within the body arrangement and configured to slide independently relative to the at least two deployable body parts between a distal position where the injection needle is covered and a proximal position where the injection needle is exposed,
wherein at least one of the at least two deployable body parts is attached at an end of a sleeve-shaped body part by at least one hinge, and
wherein at least one further hinge is provided between the at least two deployable body parts.

2. The drug delivery device according to claim 1, wherein the at least two deployable body parts are foldable or rotatable.

3. The drug delivery device according to claim 1, wherein at least one of the at least one hinge is arranged as a live hinge.

4. The drug delivery device according to claim 1, wherein at least one spring is arranged to bias the at least two deployable body parts towards the deployed state.

5. The drug delivery device according to claim 4, wherein the at least one spring is a leaf spring adapted to be curved in a relaxed state.

6. The drug delivery device according to claim 4, wherein two nested springs in the form of leaf springs are arranged, the two nested springs being curved and having a first radius in a relaxed state, wherein in a pre-stressed state the two nested springs have a second radius which is smaller than the first radius.

7. The drug delivery device according to claim 1, wherein the at least two deployable body parts are foldable or rotatable, wherein in the compact state, a main beam of the at least two deployable body parts is flush or substantially flush with the sleeve-shaped body part.

8. The drug delivery device according to claim 7, wherein the main beam is adapted to be tilted or rotated about the at least one hinge away from a longitudinal axis in the deployed state.

9. The drug delivery device according to claim 1, wherein the sleeve is configured to cover the injection needle when the at least two deployable body parts are in both the compact state and the deployed state.

10. The drug delivery device according to claim 1, wherein a distal end of the body arrangement extends beyond a distal end of the sleeve when the at least two deployable body parts are in the compact state.

11. The drug delivery device according to claim 10, wherein the distal end of the sleeve extends beyond the distal end of the body arrangement when the at least two deployable body parts are in the deployed state.

12. The drug delivery device according to claim 1, wherein the sleeve is arranged radially between the medicament container and the body arrangement.

13. The drug delivery device according to claim 1, wherein in the compact state, the at least two deployable body parts are flush or substantially flush with the sleeve-shaped body part.

14. The drug delivery device according to claim 1, wherein in the deployed state, at least one of the at least two deployable body parts is adapted to be tilted or rotated about the at least one hinge away from a longitudinal axis.

15. A drug delivery device, comprising:
a body arrangement adapted to retain a medicament container with an injection needle, the body arrangement comprising at least one deployable body part arranged to be moved from a compact state into a deployed state, wherein the at least one deployable body part in the deployed state provides an enlarged grip area compared to the compact state, and
a sleeve at least partially disposed within the body arrangement and configured to slide independently relative to the at least one deployable body part of the body arrangement between a distal position where the injection needle is covered and a proximal position where the injection needle is exposed, wherein the at least one deployable body part is foldable or rotatable, wherein at least one of the at least one deployable body part is attached at an end of a sleeve-shaped body part by at least one hinge, wherein in the compact state, the at least one deployable body part is flush or substantially flush with the sleeve-shaped body part, wherein at least one of the at least one deployable body part is adapted to be tilted or rotated about the at least one hinge away from a longitudinal axis in the deployed state, and wherein at least one further hinge is provided between at least two of the at least one deployable body parts.

16. The drug delivery device according to claim 15, wherein at least one further deployable body part is connected to an end of one of the at least one deployable body part by one of the hinges such that the at least one further deployable body part is adapted to be tilted towards the longitudinal axis relative to the at least one deployable body part.

* * * * *

UNITED STATES PATENT AND TRADEMARK OFFICE
CERTIFICATE OF CORRECTION

PATENT NO. : 11,246,988 B2
APPLICATION NO. : 16/316965
DATED : February 15, 2022
INVENTOR(S) : Cerman Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 120 days.

Signed and Sealed this
Thirteenth Day of December, 2022

Katherine Kelly Vidal
*Director of the United States Patent and Trademark Office*